(12) United States Patent
Chen et al.

(10) Patent No.: US 11,998,483 B2
(45) Date of Patent: Jun. 4, 2024

(54) ADJUSTABLE STIFFENER FOR SURGICAL INSTRUMENTS

(71) Applicant: Alcon Inc., Fribourg (CH)

(72) Inventors: Bill Chen, Irvine, CA (US); James Y. Chon, Irvine, CA (US); John R. Underwood, Laguna Nigel, CA (US)

(73) Assignee: Alcon Inc., Fribourg (CH)

( * ) Notice: Subject to any disclaimer, the term of this patent is extended or adjusted under 35 U.S.C. 154(b) by 198 days.

(21) Appl. No.: 17/115,916

(22) Filed: Dec. 9, 2020

(65) Prior Publication Data

US 2021/0177652 A1    Jun. 17, 2021

Related U.S. Application Data

(60) Provisional application No. 62/946,598, filed on Dec. 11, 2019.

(51) Int. Cl.
    *A61F 9/007*         (2006.01)
(52) U.S. Cl.
    CPC .............................. *A61F 9/00736* (2013.01)
(58) Field of Classification Search
    CPC ............. A61F 9/00736; A61F 9/00727; A61B 2017/305
    See application file for complete search history.

(56) References Cited

U.S. PATENT DOCUMENTS

| | | |
|---|---|---|
| 3,805,787 A | 4/1974 | Banko |
| 4,030,567 A | 6/1977 | Kondo |
| 5,019,035 A | 5/1991 | Missirlian |
| 5,190,050 A | 3/1993 | Nitzsche |
| 5,217,465 A | 6/1993 | Steppe |
| 5,324,306 A | 6/1994 | Makower et al. |
| 5,370,658 A | 12/1994 | Scheller |
| 5,396,880 A | 3/1995 | Kagan et al. |
| 6,312,402 B1 | 11/2001 | Hansmann |
| 6,575,989 B1 | 6/2003 | Scheller |
| 6,749,601 B2 | 6/2004 | Chin |
| 6,908,476 B2 | 6/2005 | Jud |
| 6,945,984 B2 | 9/2005 | Arumi |
| 7,207,980 B2 | 4/2007 | Christian |
| 7,338,494 B2 | 3/2008 | Ryan |
| 7,909,816 B2 | 3/2011 | Buzawa |

(Continued)

FOREIGN PATENT DOCUMENTS

| | | |
|---|---|---|
| CN | 102512284 A | 6/2012 |
| CN | 202426711 U | 9/2012 |

(Continued)

*Primary Examiner* — Sarah A Long
*Assistant Examiner* — Lindsey Bachman
(74) *Attorney, Agent, or Firm* — PATTERSON + SHERIDAN, LLP

(57) ABSTRACT

The present disclosure generally relates to microsurgical instruments having variable stiffness such as microsurgical instruments having variable stiffness for ophthalmic surgical procedures. In one embodiment, a surgical instrument includes a probe and a stiffener assembly. The stiffener assembly further includes a stiffener formed of a hollow tubular member substantially surrounding at least a portion of a length of the probe. Actuation of the stiffener along the length of the probe adjusts the stiffness of the probe, thus providing a user better control of the surgical instrument.

19 Claims, 8 Drawing Sheets

(56) References Cited

U.S. PATENT DOCUMENTS

| | | |
|---|---|---|
| 8,038,692 B2 | 10/2011 | Valencia |
| 8,187,293 B2 | 5/2012 | Kirchhevel |
| 8,202,277 B2 | 6/2012 | Ryan |
| 8,308,737 B2 | 11/2012 | Ryan |
| 8,845,666 B2 | 9/2014 | Underwood |
| 8,894,636 B2 | 11/2014 | Gille et al. |
| 9,060,841 B2 | 6/2015 | Mccawley |
| 9,138,346 B2 | 9/2015 | Scheller |
| 9,370,447 B2 | 6/2016 | Mansour |
| 9,585,788 B2 | 3/2017 | Underwood |
| 9,700,303 B2* | 7/2017 | Prior .................. A61B 17/3417 |
| 9,757,274 B2 | 9/2017 | Scheller et al. |
| 9,775,943 B2 | 10/2017 | Scheller |
| 9,795,505 B2 | 10/2017 | Yu et al. |
| 9,925,326 B2 | 3/2018 | Scheller |
| 9,931,244 B2 | 4/2018 | Ryan |
| 9,949,876 B2 | 4/2018 | Mansour |
| 10,045,883 B2 | 8/2018 | Egli |
| 10,085,883 B2 | 10/2018 | Auld |
| 10,179,007 B2* | 1/2019 | Peterson |
| 10,285,583 B2 | 5/2019 | Parto |
| 10,376,315 B2 | 8/2019 | Scheller et al. |
| 10,391,232 B2 | 8/2019 | Scheller et al. |
| 10,413,445 B2 | 9/2019 | Scheller et al. |
| 10,413,446 B2 | 9/2019 | Bouch et al. |
| 10,617,560 B2 | 4/2020 | Ryan |
| 10,639,197 B2 | 5/2020 | Lopez |
| 10,675,181 B2 | 6/2020 | Murakami |
| 10,828,192 B2 | 11/2020 | Scheller et al. |
| 10,898,373 B2 | 1/2021 | Ryan |
| 10,945,882 B2 | 3/2021 | Ryan |
| 11,020,270 B1 | 6/2021 | Peyman |
| 11,278,449 B2 | 3/2022 | Ryan |
| 2003/0195539 A1 | 10/2003 | Attinger |
| 2005/0033309 A1 | 2/2005 | Ryan |
| 2005/0209618 A1 | 9/2005 | Auld |
| 2007/0099149 A1 | 5/2007 | Levy et al. |
| 2007/0106300 A1 | 5/2007 | Auld |
| 2007/0255196 A1 | 11/2007 | Wuchinich |
| 2008/0195135 A1* | 8/2008 | Attinger .............. A61F 9/00736 606/185 |
| 2008/0255526 A1 | 10/2008 | Bosse et al. |
| 2009/0093800 A1 | 4/2009 | Auld |
| 2009/0131870 A1 | 5/2009 | Fiser |
| 2010/0063359 A1 | 3/2010 | Okoniewski |
| 2010/0228226 A1 | 9/2010 | Nielsen |
| 2012/0116361 A1* | 5/2012 | Hanlon .................. A61F 9/007 606/1 |
| 2013/0090531 A1 | 4/2013 | Ryan |
| 2013/0090635 A1 | 4/2013 | Mansour |
| 2013/0165951 A1* | 6/2013 | Blake, III .......... A61B 17/1285 606/143 |
| 2013/0281817 A1 | 10/2013 | Schaller |
| 2014/0121469 A1 | 5/2014 | Meckel et al. |
| 2014/0128896 A1 | 5/2014 | Ryan |
| 2015/0231687 A1 | 8/2015 | Ookubo et al. |
| 2016/0310322 A1* | 10/2016 | Schaller |
| 2017/0215855 A1 | 8/2017 | Nunan |
| 2017/0333251 A1 | 11/2017 | Scheller et al. |
| 2018/0214307 A1 | 8/2018 | Ryan |
| 2018/0228651 A1 | 8/2018 | Mansour |
| 2018/0250164 A1 | 9/2018 | Ryan |
| 2018/0360660 A1 | 12/2018 | Lopez |
| 2019/0059936 A1 | 2/2019 | Ryan |
| 2019/0269556 A1 | 9/2019 | Meckel |
| 2019/0282322 A1 | 9/2019 | Mirsepassi |
| 2020/0163717 A1 | 5/2020 | Hartkopf-ceylan |
| 2020/0197217 A1 | 6/2020 | Ryan |
| 2021/0177652 A1 | 6/2021 | Chen et al. |
| 2021/0177653 A1 | 6/2021 | Hallen |
| 2021/0244567 A1 | 8/2021 | Ryan |
| 2021/0251805 A1 | 8/2021 | Ryan |
| 2021/0290438 A1 | 9/2021 | Hallen |
| 2022/0031509 A1 | 2/2022 | Tazawa |
| 2022/0192706 A1 | 6/2022 | Grueebler et al. |

FOREIGN PATENT DOCUMENTS

| | | |
|---|---|---|
| CN | 207755450 U | 8/2018 |
| DE | 651436 C | 10/1937 |
| EP | 1955684 A1 | 8/2008 |
| EP | 2760400 B1 | 1/2018 |
| EP | 3319564 B1 | 11/2019 |
| EP | 3191161 B1 | 1/2020 |
| EP | 3656332 A1 | 5/2020 |
| EP | 3352682 B1 | 7/2020 |
| EP | 3332756 B1 | 8/2020 |
| GB | 1448129 A | 9/1976 |
| JP | 2009072221 A | 4/2009 |
| JP | 2020044289 A | 3/2020 |
| JP | 2022040303 A | 3/2022 |
| RU | 2525735 C1 | 8/2014 |
| WO | 0119255 A1 | 3/2001 |
| WO | 2010064670 A1 | 6/2010 |
| WO | 2013133712 A1 | 9/2013 |
| WO | 2017053832 A1 | 3/2017 |
| WO | 2017075514 A1 | 5/2017 |

* cited by examiner

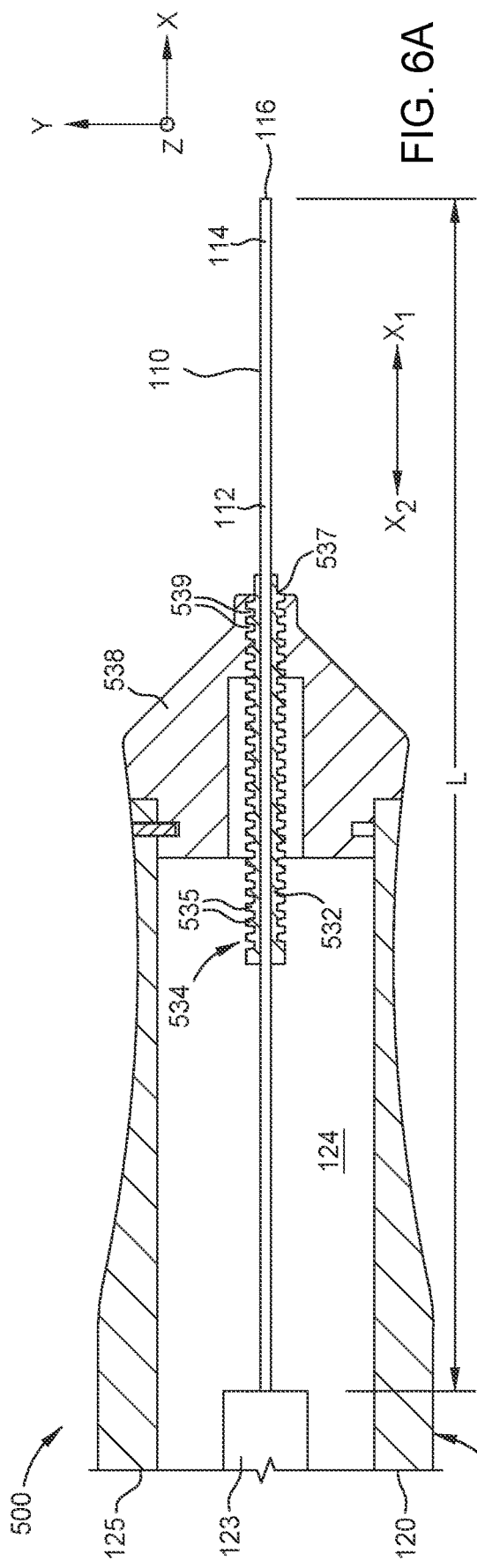
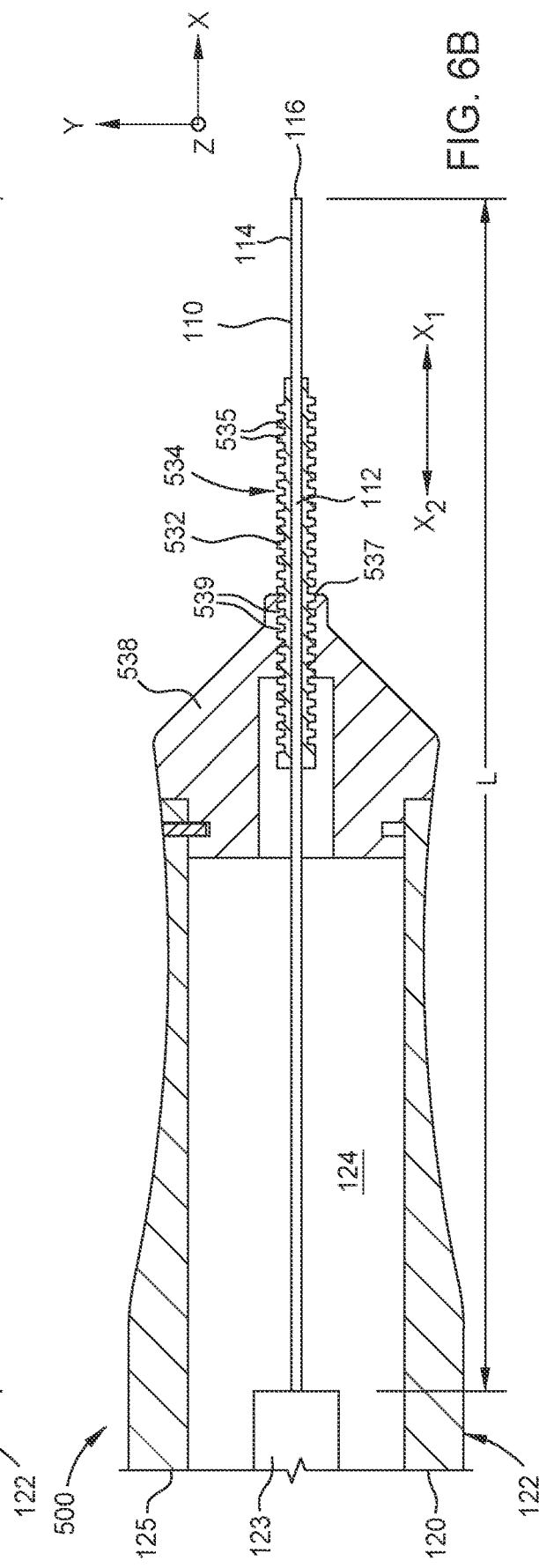

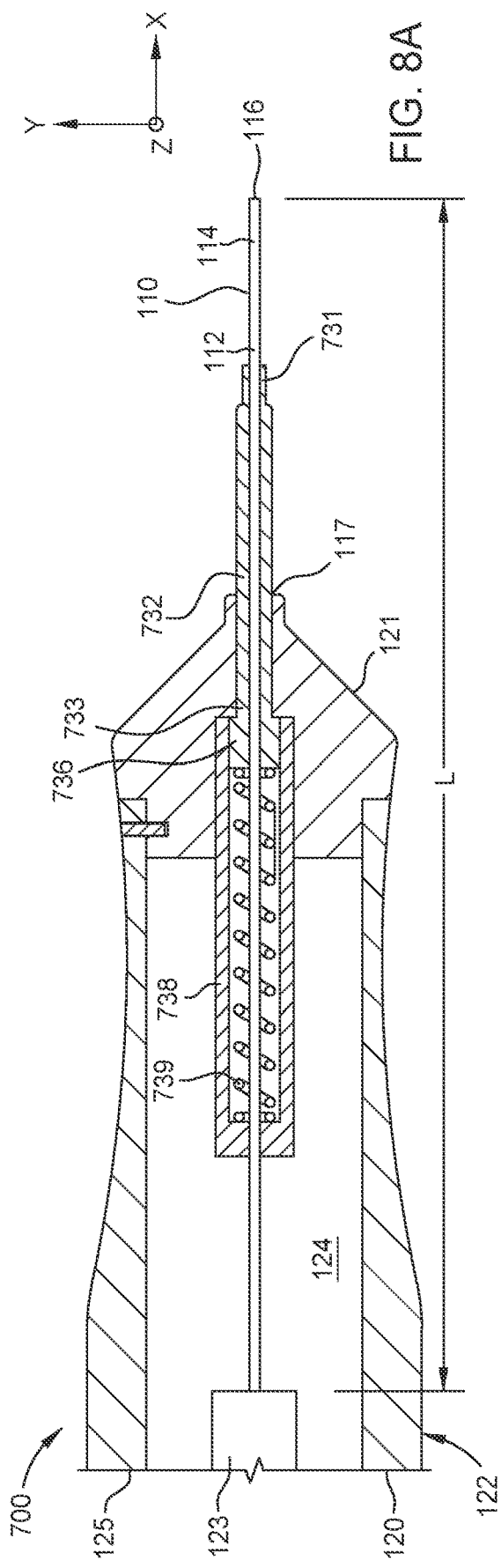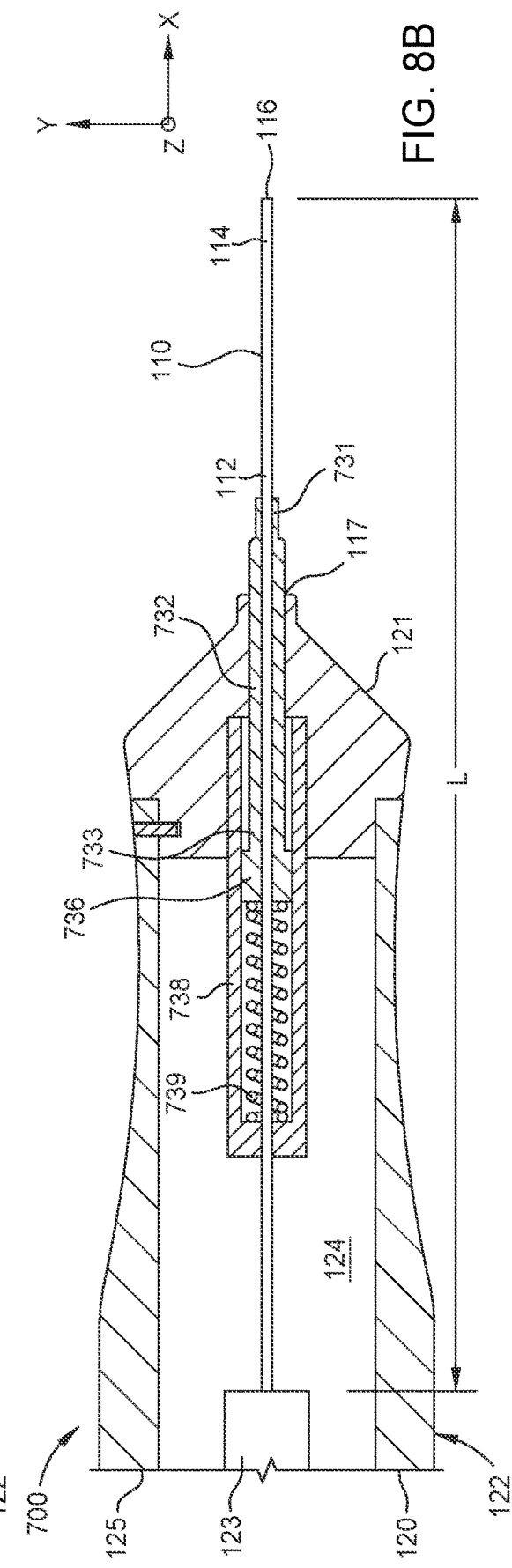

ADJUSTABLE STIFFENER FOR SURGICAL INSTRUMENTS

PRIORITY CLAIM

This application claims the benefit of priority of U.S. Provisional Patent Application Ser. No. 62/946,598 titled "ADJUSTABLE STIFFENER FOR SURGICAL INSTRUMENTS," filed on Dec. 11, 2019, whose inventors are Bill Chen, James Y. Chon and John R. Underwood, which is hereby incorporated by reference in its entirety as though fully and completely set forth herein.

DESCRIPTION OF THE RELATED ART

Continuous efforts to minimize the invasiveness of surgical procedures, such as ophthalmic surgical procedures, have led to the development of small-gauge surgical instrumentation for microincision techniques. Small gauge vitrectomy, also known as minimally invasive vitreous surgery (MIVS), is a classic example of one such type of surgical procedure utilizing small-gauge instrumentation. Examples of common ocular conditions that may be treated by minimally invasive vitreous surgery include retinal detachment, macular holes, premacular fibrosis, and vitreous hemorrhages. The benefits associated with modern MIVS as compared to more invasive vitrectomies include access to greater pathology, greater fluidic stability, increased patient comfort, less conjunctival scarring, less postoperative inflammation, and earlier visual recovery, among others. Accordingly, indications for MIVS and other microincision techniques have expanded in recent years.

Despite the aforementioned benefits of microincision techniques and their widespread acceptance, there remain numerous challenges with the utilization of small-gauge surgical instruments, particularly in the field of ophthalmology. One commonly noted concern among surgeons is instrument rigidity. The smaller diameter of these microincision instruments, such as vitrectomy probes, causes decreased stiffness thereof, making it difficult for surgeons to control the instruments during certain ocular surgical procedures. With small gauge ophthalmic surgical instruments, for example, the instrument tips can move in unintended directions at the extreme limits of the eye, thus making delicate procedures such as the peeling of membranes from the retinal surface extremely difficult.

Accordingly, what is needed in the art are improved methods and apparatus for minimally-invasive ophthalmic surgical procedures.

SUMMARY

In one embodiment, a surgical instrument is provided with a base unit, a probe, and a stiffener assembly. The base unit is configured to be held by a user. The probe is disposed through a first opening in a distal end of the base unit and has a length parallel to a longitudinal axis thereof. The stiffener assembly includes a stiffener extending through the first opening in the base unit and an actuation mechanism configured to actuate the stiffener along the length of the probe. The stiffener is formed of a hollow tubular member that surrounds at least a portion of the probe and is slidably coupled thereto.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 6A illustrates a schematic cross-sectional side view of the instrument of FIG. 5.

FIG. 6B illustrates another schematic cross-sectional side view of the instrument of FIG. 5.

FIG. 8A illustrates a schematic cross-sectional side view of the instrument of FIG. 7.

FIG. 8B illustrates another schematic cross-sectional side view of the instrument of FIG. 7.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to microsurgical instruments having variable stiffness, and more particularly, microsurgical instruments having variable stiffness for ophthalmic surgical procedures. In one embodiment, a surgical instrument includes a probe and a stiffener assembly. The stiffener assembly further includes a stiffener formed of a hollow tubular member substantially surrounding at least a portion of a length of the probe. Actuation of the stiffener along the length of the probe adjusts the stiffness of the probe, thus providing a user better control of the surgical instrument.

Figure 1:
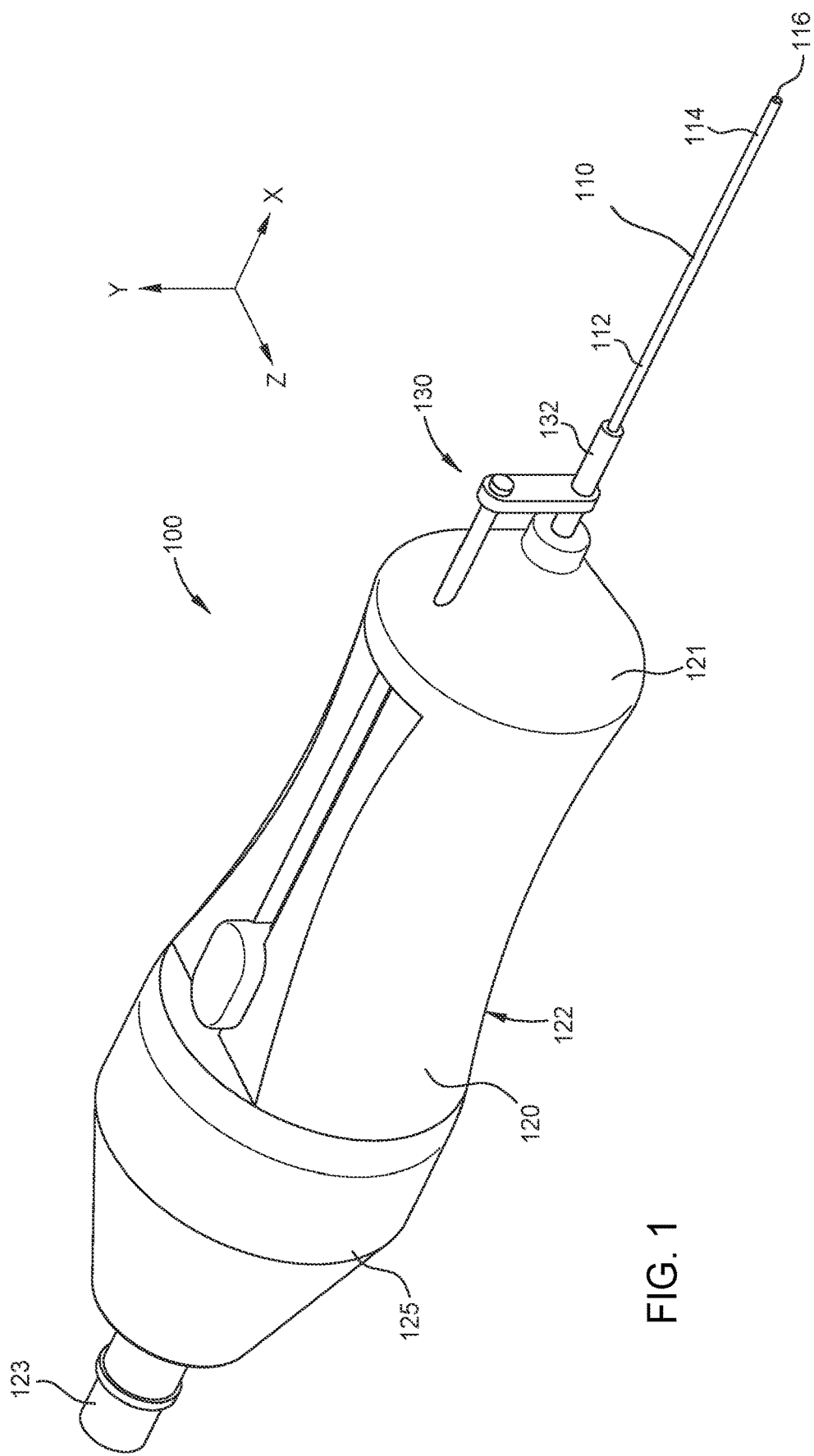
FIG. 1 illustrates a perspective view of an exemplary instrument according to one embodiment of the present disclosure.

FIG. 1 illustrates a perspective view of an exemplary instrument 100 according to one embodiment described herein. As depicted in FIG. 1, the instrument 100 comprises a probe or needle 110 (referred to hereinafter as a "probe") and a base unit 120. The probe 110 includes a proximal portion 112 and a distal portion 114 which terminates distally at the distal end 116. In some embodiments, the proximal portion 112 extends through a substantial portion of an interior chamber (124, shown in FIGS. 2A and 2B) of the base unit 120.

In one example, the probe 110 is an elongated cutting member of a vitrectomy probe. For example, the probe 110 may be inserted into a cannula for performance of vitreous surgery, which may be aspirating or non-aspirating. The probe 110 may comprise a hollow tube having a diameter less than about 20 gauge. For example, the probe 110 has a diameter less than about 23 gauge, such as a diameter less than about 25 gauge. In one embodiment, the probe 110 has a diameter of approximately 27 gauge. In further examples, the probe 110 may include an illumination device, a laser guide, a suction device, forceps, scissors, retractors, or other suitable devices disposed therein or coupled thereto.

Generally, the probe 110 is formed of a material suitable for minimally invasive surgical procedures, such as vitreo-retinal surgeries that involve removal of the vitreous in the eye, or other surgical procedures. For example, the probe 110 is formed of surgical grade stainless steel, aluminum, or titanium.

The probe 110 is partially and longitudinally disposed through a distal end 121 of the base unit 120 adjacent the proximal portion 112 and may be directly or indirectly attached thereto within the interior chamber of the base unit 120 (interior chamber 124, as discussed below). In one embodiment, the base unit 120 is a handpiece having an outer surface 122 configured to be held by a user, such as a surgeon. For example, the base unit 120 may be contoured to substantially fit the hand of the user. In some embodiments, the outer surface 122 may be textured or have one or more gripping features formed thereon, such as one or more grooves and/or ridges.

The base unit 120 may house at least a portion of a drive mechanism operable to reciprocate the probe 110 within and relative to the base unit 120. In one example, the drive mechanism may be a pneumatic drive mechanism including a diaphragm. The base unit 120 may further provide one or more ports 123 at a proximal end 125 thereof for one or more supply lines to be routed into the interior chamber 124. For example, the one or more ports 123 may provide a connection between the base unit 120 and a vacuum source for aspiration. In another example, the one or more ports 123 provides a connection to a pneumatic, hydraulic, or electrical power source to operate the drive mechanism, an illumination device, a laser, or other suitable device within or coupled to the base unit 120.

The instrument 100 further includes a stiffener assembly 130 comprising a stiffener 132 slidably coupled to and substantially surrounding at least a portion of the probe 110. The stiffener 132 is adjustable relative to the probe 110, enabling a user to position the stiffener 132 (e.g., a distal end of the stiffener 132) at different points along a length L (shown in FIGS. 2A and 2B) of the probe 110 exterior to the base unit 120. Accordingly, a user may selectively adjust the level of stiffness of the probe 110 by re-positioning the stiffener 132 relative to the distal end 116, thereby manipulating the amount of support provided to the probe 110 and stabilizing the instrument 100 during use thereof.

Figure 2A:
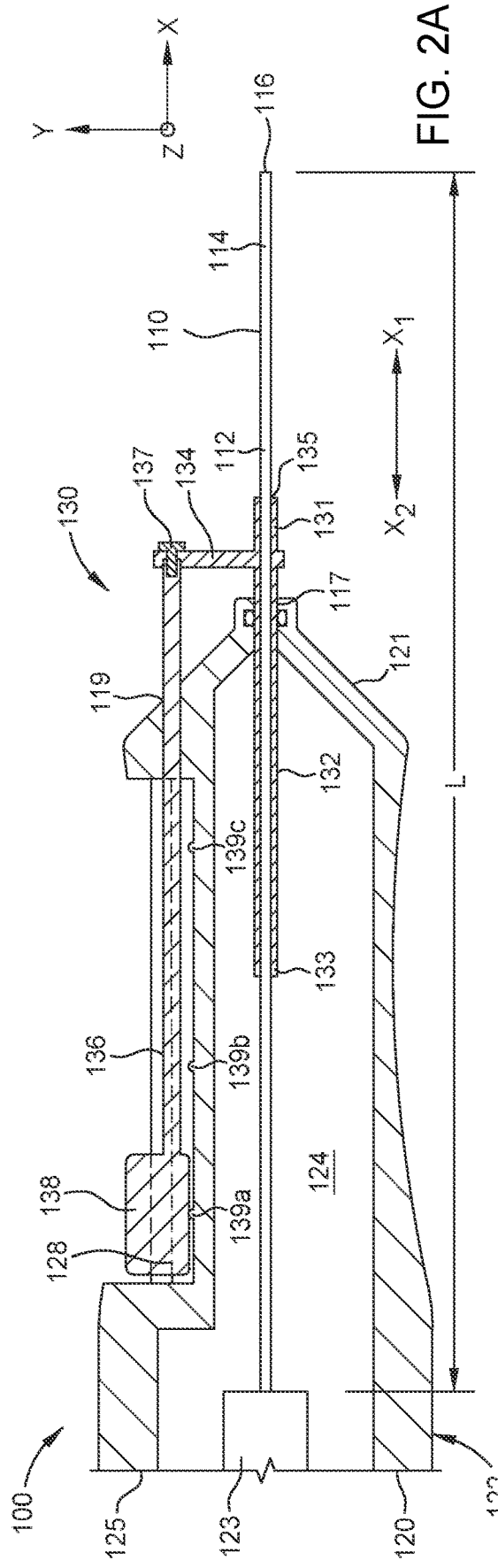
FIG. 2A illustrates a schematic cross-sectional side view of the instrument of FIG. 1.
Figure 2B:
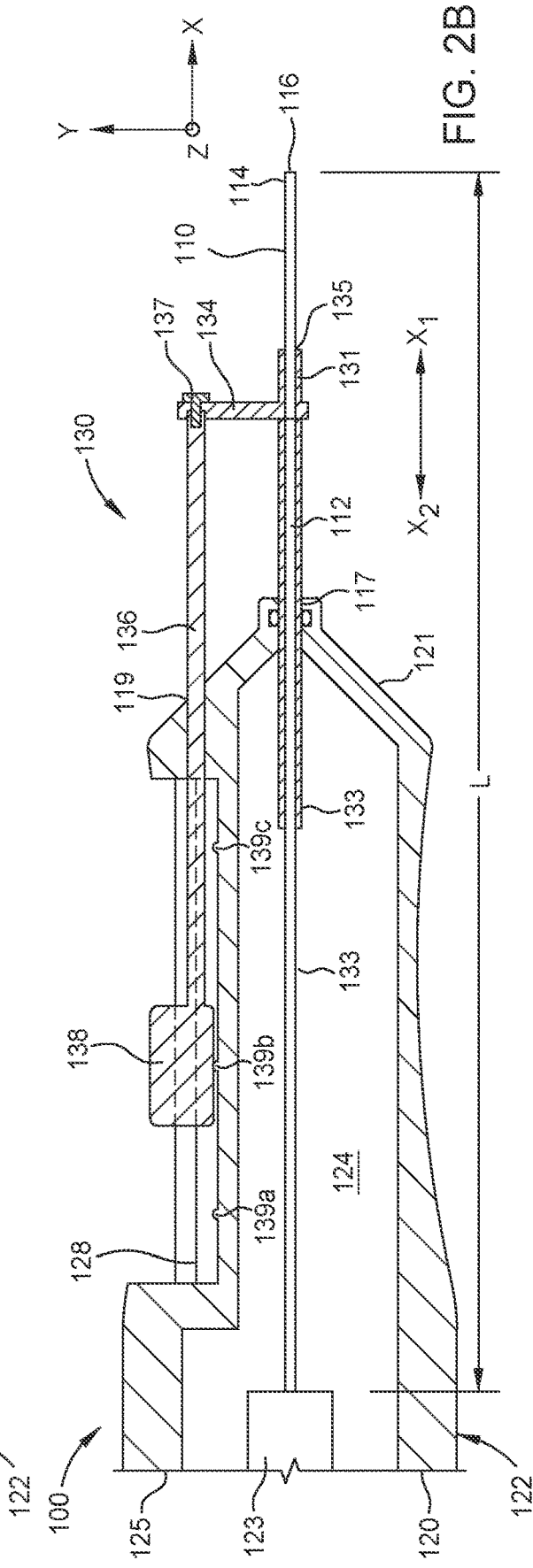
FIG. 2B illustrates another schematic cross-sectional side view of the instrument of FIG. 1.

FIGS. 2A and 2B illustrate schematic cross-sectional views of the instrument 100 with the stiffener 132 positioned at different points along a length L of the probe 110. Therefore, FIGS. 2A and 2B are herein described together with FIG. 1 for clarity. The stiffener 132 is generally a cylindrical and hollow tube substantially surrounding the probe 110 at or near the proximal portion 112. Similar to the probe 110, the stiffener 132 is formed of a material suitable for minimally invasive surgical procedures, such as vitreo-retinal surgeries and other surgical procedures. In some embodiments, the stiffener 132 is formed of a metallic material, such as surgical grade stainless steel, aluminum, or titanium. In other embodiments, the stiffener 132 is formed of a composite material, such as a polymer composite material or a ceramic composite material.

Along with the probe 110, the stiffener 132 is disposed through an opening 117 of the distal end 121 and has a proximal end 133 disposed in the interior chamber 124. The stiffener 132 is sized to possess an axial length sufficient to provide a desired rigidity and stability to the probe 110 while having a portion thereof still remaining in the interior chamber 124 when the stiffener assembly 130 is in a (e.g., fully) protracted position. For example, the stiffener 132 may have an axial length between about 0.25 inches and about 1.75 inches, such as between about 0.30 inches and about 1.50 inches. For example, the stiffener 132 may have an axial length between about 0.50 inches and about 1.25 inches.

In one embodiment, stiffener 132 has a uniform outer diameter from the distal end 131 to the proximal end 133. Having a uniform outer diameter enables a substantial length of the stiffener 132 to be reciprocated through the opening 117 without forming an airgap therebetween. However, other shapes and morphologies of the stiffener 132 are also contemplated. For example, in some embodiments, the stiffener 132 comprises a square, rectangular, or polygonal tube. In further embodiments, the stiffener 132 may have a non-uniform outer diameter. For example, the stiffener 132 may have an outer diameter having one or more dimensions following a step-wise or gradual delta.

An inner cavity 135 of the stiffener 132 is sized to accommodate the outer diameter of the probe 110 while also permitting the stiffener 132 to be readily moved along probe 110. Thus, an inner diameter or width of the stiffener 132 is greater than the outer diameter of the probe 110 and enables a sliding fit. In one embodiment, a radial clearance between the stiffener 132 and the probe 110 is between about 0.00020 inches and about 0.00060 inches, such as between about 0.00025 inches and about 0.00050 inches. For example, the radial clearance between the stiffener 132 and the probe 110 is between about 0.00030 inches and about 0.00040 inches, such as about 0.00035 inches. Further, the inner dimensions of the stiffener 132 may be uniform from the distal end 131 to the proximal end 133 to enable uniform stabilization of the probe 110 throughout the inner cavity of the stiffener 132.

In one embodiment, the stiffener 132 is indirectly coupled to the control element 138 by the coupling arm 134 and the rod 136. The coupling arm 134 connects the stiffener 132 to the rod 136 and is oriented in a non-parallel fashion therebetween. In some embodiments, the coupling arm 134 is a direct extension of the stiffener 132 and/or the rod 136. That is, the coupling arm 134 and the stiffener 132 and/or the rod 136 are a single integral component. In other embodiments, the coupling arm 134 and the stiffener 132 and/or the rod 136 are separate components coupled to one another by one or more coupling mechanisms and/or adhesives. For example, as depicted in FIGS. 2A and 2B, the coupling arm 134 and the rod 136 are coupled together by a pin 137. In other examples, the coupling arm 134 and the rod 136 may be snap-fit together.

The control element 138 may be a button, knob, switch, toggle, or any other suitable device capable of being actuated by a user. As depicted in FIGS. 2A and 2B, the control element 138 is partially disposed within a linear channel 128 formed in the base unit 120. The channel 128 runs substantially parallel to the probe 110 and enables bidirectional sliding of the control element 138 along a longitudinal axis X thereof. In one embodiment, the rod 136 is directly coupled to the control element 138 and runs substantially parallel to the probe 110 within the channel 128. The rod 136 may further be disposed through a second opening 119 formed in the distal end 121 of the base unit 120 in order to connect with the coupling arm 134. Generally, the rod 136 may be formed of a metallic or composite material. In some embodiments, the rod 136 is formed of stainless steel, aluminum, or titanium. In other embodiments, the rod 136 is formed of a polymer composite material or ceramic composite material.

During use, the rod 136 transfers motion of the control element 138 to the coupling arm 134, and thus, the stiffener 132. Accordingly, sliding of the control element 138 within the channel 128 results in sliding of the stiffener 132 along the length L of the probe 110. In some embodiments, the stiffener 132 is adjustable up to a distance of about 15 mm along the length L of the probe 110, such as a distance up to about 10 mm along the length L of the probe 110. For example, the stiffener 132 is adjustable up to a distance of about 5 mm along the length L of the probe 110.

In one embodiment, the channel 128 comprises a track having one or more protrusions 139 disposed at preset locations along a length of the channel 128 upon which the control element 138 may be secured. For example, the control element 138 may have a groove disposed on a lower or oblique surface thereof and matching the morphology of the one or more protrusions 139. Thus, the control element 138 may be locked upon a protrusion 139 by sliding the control element 138 adjacent thereto and engaging the groove with the protrusion 139. As a result, the one or more protrusions 139 may be utilized to provide predetermined levels of rigidity to the probe 110. That is, the one or more protrusions 139 may be located at preset increments along the length of the channel 128 corresponding to predetermined levels of rigidity provided to the probe 110.

In another embodiment, the channel 128 comprises a track with substantially planar surfaces upon which the control element 138 may be slidably and dynamically actuated by the user, providing greater flexibility and freedom to the user in determining a desired position of the stiffener 132 relative to the probe 110. Accordingly, the user may set the control element 138 at a desired position by simply controlling the control element 138 with their thumb.

FIGS. 2A and 2B illustrate the channel 128 having three protrusions 139a-139c disposed therein. Generally, sliding the stiffener 132 towards the distal end 116 of the probe 110 increases the rigidity of the probe 110. In FIG. 2A, the stiffener assembly 130 is disposed in a fully retracted position where the control element 138 is locked in place over the protrusion 139a. Accordingly, a majority of the stiffener 132 is retracted within the base unit 120, providing decreased stability and rigidity to the probe 110. In FIG. 2B, the stiffener assembly 130 is disposed in a protracted position wherein the control element 138 is locked in place over the protrusion 139b. Accordingly, a greater portion of the stiffener 132 is protracted over the proximal portion 112 of the probe 110, providing increased stability and rigidity to the probe 110.

Although the stiffener assembly 130 is depicted and described as having the control element 138, the coupling arm 134, and the rod 136, these elements comprise only one embodiment of an actuation mechanism for a stiffener and thus should not be considered limiting thereof. Additional embodiments and configurations of actuation mechanisms for a stiffener are further described below.

Figure 3:
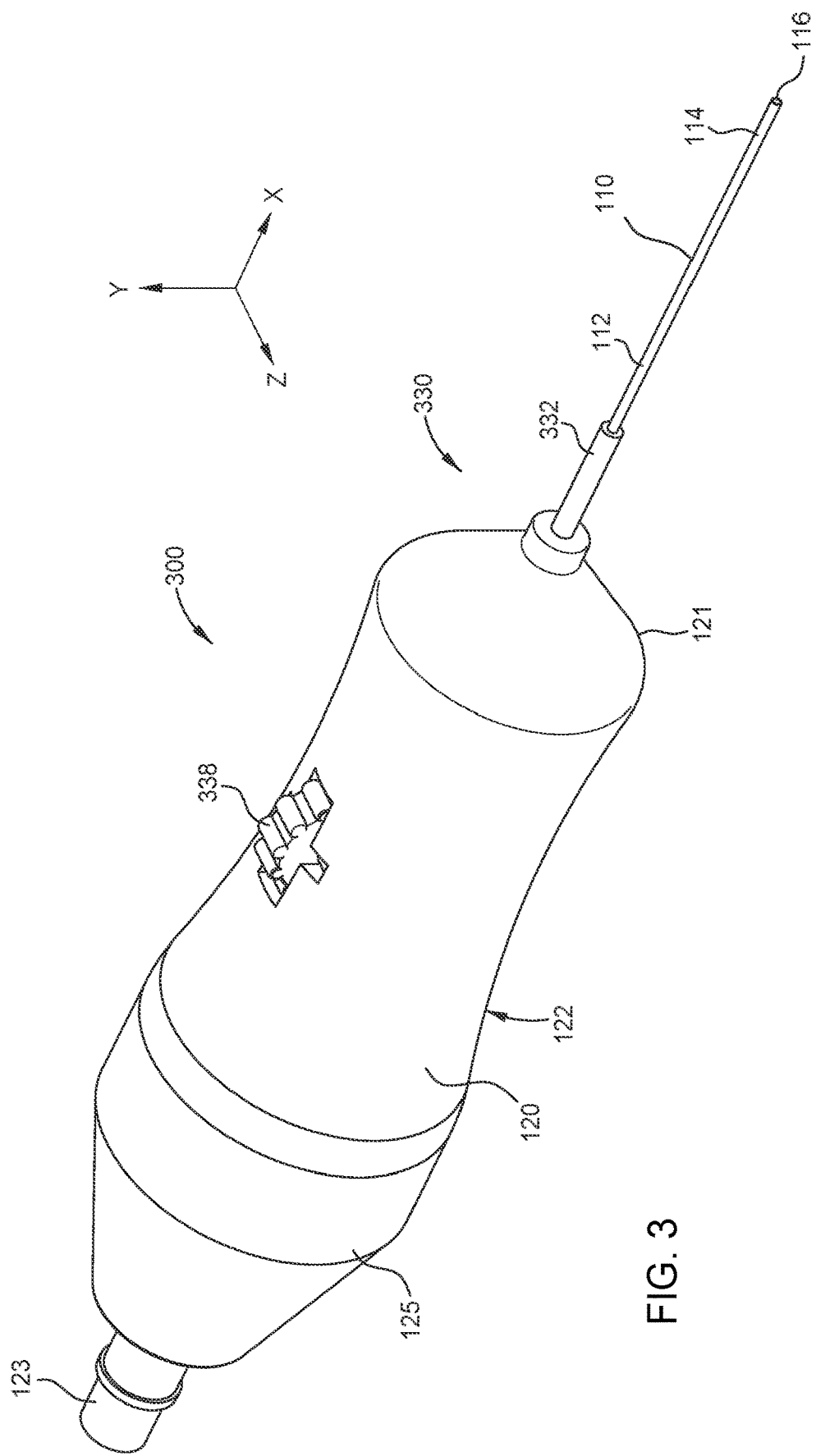
FIG. 3 illustrates a perspective view of an exemplary instrument according to one embodiment of the present disclosure.

FIG. 3 illustrates a perspective view of another exemplary instrument 300 having a stiffener assembly 330. The instrument 300 is substantially similar to the instrument 100, except for the structure and actuating mechanism of the stiffener assembly 330. As depicted in FIG. 3, the stiffener assembly 330 includes a pinion 338 operatively engaged with a proximal end (e.g., proximal end 333, discussed below) of a stiffener 332 within the interior chamber 124 (shown in FIGS. 4A and 4B) to actuate the stiffener 332 along the probe 110.

Figure 4A:
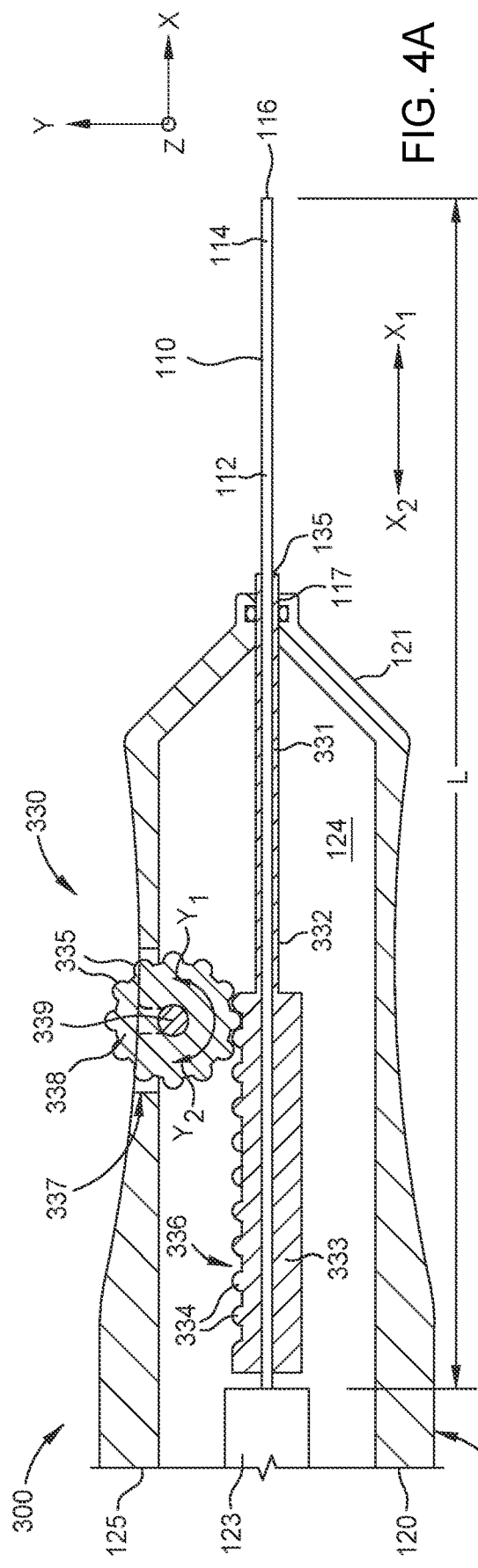
FIG. 4A illustrates a schematic cross-sectional side view of the instrument of FIG. 3.
Figure 4B:
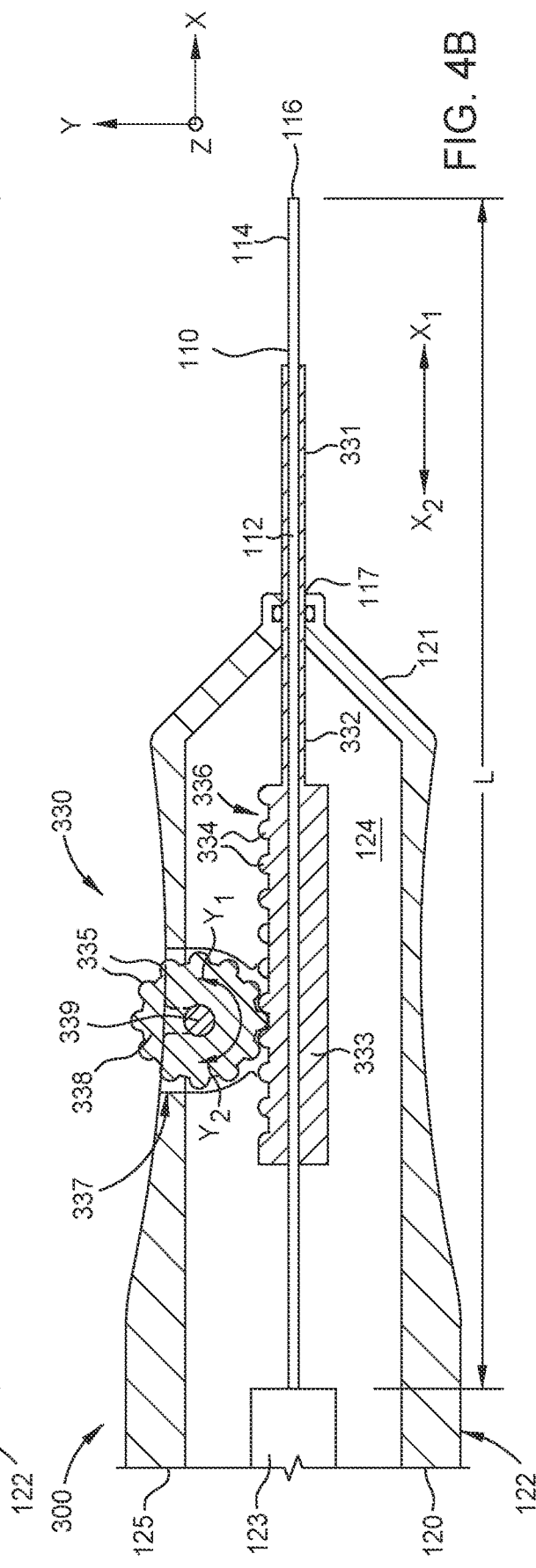
FIG. 4B illustrates another schematic cross-sectional side view of the instrument of FIG. 3.

FIGS. 4A and 4B illustrate schematic cross-sectional views of the exemplary instrument 300 with the stiffener 332 positioned at different points along the length L of the probe 110. Therefore, FIGS. 4A and 4B are herein described together with FIG. 3 for clarity.

As described above, the stiffener assembly 330 includes the stiffener 332 and the pinion 338. Similar to the stiffener 132, the stiffener 332 is substantially a hollow tube slidably mounted to and surrounding the probe 110. Along with the probe 110, the stiffener 332 is disposed through the opening 117 in the base unit 120 and extends into the interior chamber 124 thereof. Unlike the stiffener 132, however, the stiffener 332 includes the proximal end 333 having a rack 336 formed thereon and engaged with the pinion 338. In one embodiment, the proximal end 333 is integrally coupled to a distal end 331 thereof. In another embodiment, the proximal end 333 is removably coupled to the distal end 331 via any suitable coupling mechanism and/or adhesive. The stiffener 332, including the proximal end 333, is sized to possess an axial length sufficient to provide a desired rigidity and stability to the probe 110 when the stiffener assembly 330 is in a (e.g., fully) protracted position. For example, the stiffener 332 may have an axial length between about 0.25 inches and about 1.75 inches, such as between about 0.30 inches and about 1.50 inches. For example, the stiffener 132 may have an axial length between about 0.50 inches and about 1.25 inches.

The rack 336 includes a first plurality of linear gear teeth 334 formed on an outer surface of the proximal end 333 and operatively engaged with a second plurality of teeth 335 formed on the pinion 338. A linear pitch between each of the plurality of linear gear teeth 334 is dependent on a diameter of the pinion 338. In one example, the pitch between each of the plurality of linear gear teeth 334 is between about 0.025 inches and about 0.25 inches, such as between about 0.05 inches and about 0.20 inches. For example, the pitch between each of the plurality of linear gear teeth 334 is between about 0.075 inches and about 0.15 inches, such as between about 0.090 inches and about 0.10 inches. Generally, the rack 336 is formed of a metallic or composite material. In some embodiments, the rack 336 is formed of stainless steel, aluminum, or titanium. In other embodiments, the rack 336 is formed of a polymer composite material or ceramic composite material.

The pinion 338 is disposed in a recess 337 (e.g., opening) formed in the outer surface 122 of the base unit 120 such that a first portion of the pinion 338 protrudes from the recess 337 towards an exterior of the base unit 120 and is diametrically opposed to a second portion of the pinion 338 engaged with the rack 336 within the interior chamber 124. Similar to the rack 336, the pinion 338 is formed of a metallic or composite material, such as stainless steel, aluminum, titanium, polymer composite, or ceramic composite. The recess 337 may be formed in any suitable location along the outer surface 122. For example, the recess 337 may be disposed adjacent either the distal end 121 or the proximal end 125 of the base unit. In other embodiments, the recess 337 may be more centrally disposed between the distal end 121 and the proximal end 125.

In one embodiment, the pinion 338 is rotatably supported within the recess 337 by a pin 339 rotatably coupled to the base unit 120. Accordingly, rotation of the pinion 338 about an axis Z normal to the longitudinal axis X linearly actuates the stiffener 332 along the length L of the probe 110 in a first or second direction, X1 and X2, respectively. For example, as depicted in FIGS. 4A and 4B, rotation of the pinion 338 in a first rotational direction Y1 actuates the stiffener 332 in the first linear direction X1 along the probe 110, thus protracting the stiffener 332 from within the interior chamber 124 of the base unit 120 and increasing the rigidity of the probe 110. Conversely, rotation of the pinion 338 in a second rotational direction Y2 actuates the stiffener 332 in the second linear direction X2 along the probe 110, thus retracting the stiffener 332 into the base unit 120 and reducing the rigidity of the probe 110. In some embodiments, the stiffener 332 is adjustable up to a distance of about 15 mm along the length L of the probe 110, such as a distance up to about 10 mm along the length L of the probe 110. For example, the stiffener 332 is adjustable up to a distance of about 5 mm along the length L of the probe 110.

Although the stiffener assembly 330 is depicted and described as having the pinion 338 and the rack 336, these elements comprise only one embodiment of an actuation mechanism for a stiffener and thus should not be considered limiting thereof. Additional embodiments and configurations of actuation mechanisms for a stiffener are further described throughout this application.

Figure 5:
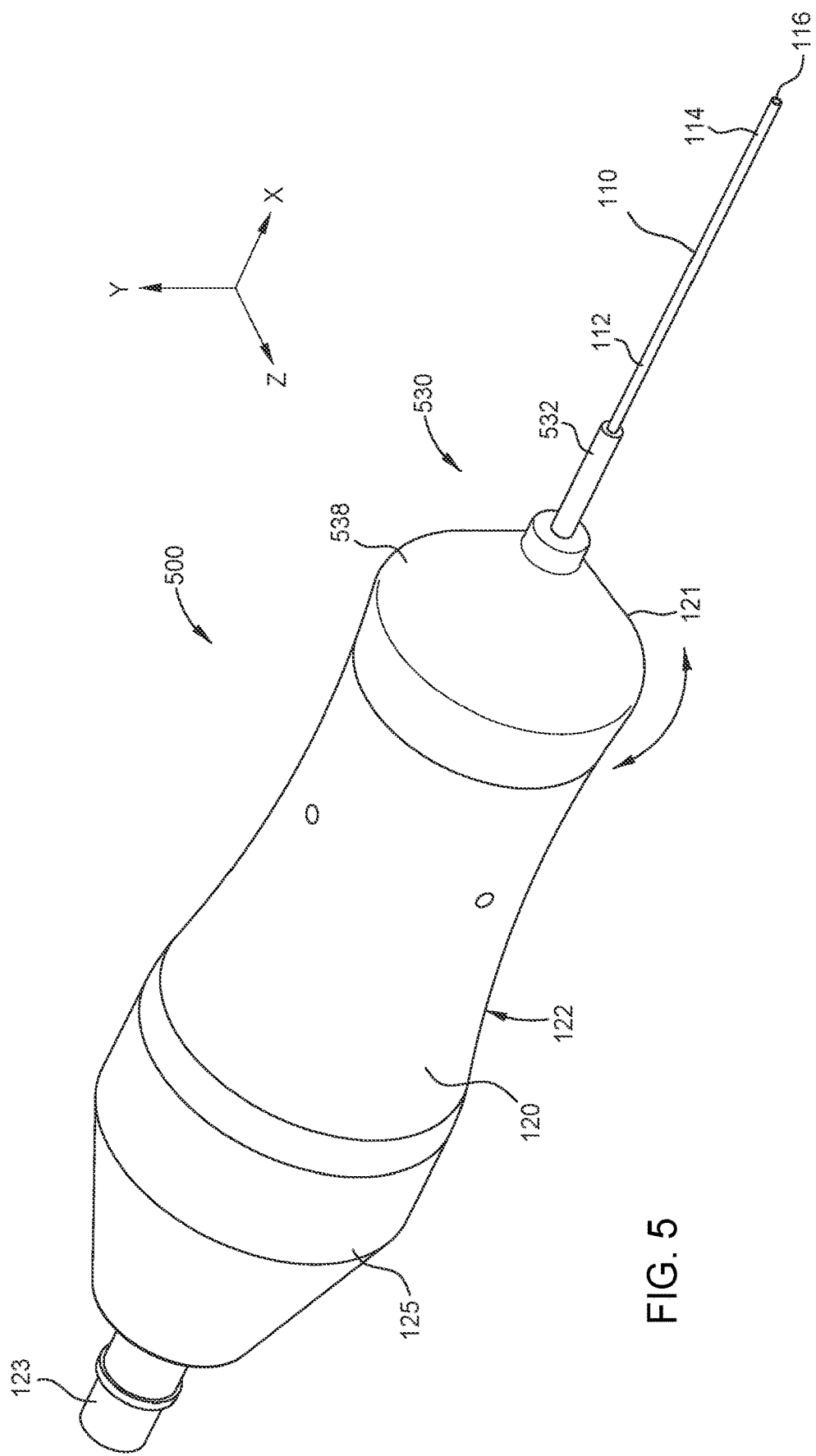
FIG. 5 illustrates a perspective view of an exemplary instrument according to one embodiment of the present disclosure.

FIG. 5 illustrates a perspective view of another exemplary instrument 500 according to one embodiment described herein. The instrument 500 is substantially similar to the instruments 100 and 300, except for the structure and actuating mechanism of stiffener assembly 530. As depicted in FIG. 5, the stiffener assembly 530 includes a rotatable distal end 538 movingly coupled to the stiffener 532 to actuate the stiffener 532 along the probe 110.

FIGS. 6A and 6B illustrate schematic cross-sectional views of the exemplary instrument 500 with the stiffener 532 positioned at different points along the length L of the probe 110. Therefore, FIGS. 6A and 6B are herein described together with FIG. 5 for clarity.

As described above, the stiffener assembly 530 includes the stiffener 532 and the rotatable distal end 538. The distal end 538 is rotatably coupled to the base unit 120 and configured to rotate about the longitudinal axis X through the opening 537. The distal end 538 is typically formed of a metallic or composite material. In some embodiments, the distal end 538 is formed of stainless steel, aluminum, or titanium. In other embodiments, the distal end 538 is formed of a polymer composite material or ceramic composite material.

Similar to the stiffeners 132 and 332, the stiffener 532 is generally a hollow tube slidably mounted to and substantially surrounding the probe 110 adjacent the proximal portion 112. Along with the probe 110, the stiffener 532 is disposed through the opening 537 in the distal end 538 and extends into the interior chamber 124 thereof. The stiffener 532 is sized to possess an axial length sufficient to provide a desired rigidity and stability to the probe 110 while having a portion thereof still extending through the opening 537 when the stiffener assembly 530 is in a (e.g., fully) protracted position. For example, the stiffener 532 may have an axial length between about 0.25 inches and about 1.75 inches, such as between about 0.30 inches and about 1.50 inches. For example, the stiffener 132 may have an axial length between about 0.50 inches and about 1.25 inches.

The stiffener 532 has one or more features 535 formed on an exterior surface 534 thereof. In one embodiment, the features 535 include a spiraling thread. In another embodiment, the features 535 include one or more protrusions and/or grooves formed on the exterior surface 534. The features 535 of the stiffener 532 are operatively engaged with one or more features 539 formed on an interior surface of the opening 537. Similar to the features 535, the features 539 may include protrusions, grooves, and/or a spiraling thread. However, at least one of the opening 537 and the exterior surface 534 has a spiraling thread formed thereon. Generally, the features 535 of the stiffener 532 are female mating features and the features 539 of the opening 537 are male mating features. However, it is also contemplated that the features 535 may be male mating features and the features 539 may be female mating features.

Accordingly, rotation of the distal end 538 about the longitudinal axis X linearly actuates the stiffener 532 along the length L of the probe 110 in a first or second direction X1 and X2, respectively. For example, rotation of the distal end 538 in a first rotational direction around the longitudinal axis X may actuate the stiffener 532 in the first linear direction X1 along the probe 110, thus protracting the stiffener 532 from the interior chamber 124 of the base unit 120 and increasing the rigidity of the probe 110. Conversely, rotation of the distal end 538 in a second rotational direction around the longitudinal axis X may actuate the stiffener 532 in the second linear direction X2 along the probe 110, thus retracting the stiffener 532 into the base unit 120 and reducing the rigidity of the probe 110. In some embodiments, the stiffener 532 is adjustable up to a distance of about 15 mm along the length L of the probe 110, such as a distance up to about 10 mm along the length L of the probe 110. For example, the stiffener 532 is adjustable up to a distance of about 5 mm along the length L of the probe 110. Note that, in the embodiments described herein, at least a portion (e.g., distal portion 114) of probe 110 is inserted into a patient's eye through an insertion cannula. However, the remainder (e.g., proximal portion 112) of the probe remains outside of the eye and the insertion cannula. When in a (e.g., fully) protracted state, the stiffeners described herein cover the portion of the probe that remains outside of the eye and the insertion cannula (or the hub of the insertion cannula).

Although the stiffener assembly 530 is depicted and described as having the rotatable distal end 538, this element comprises only one embodiment of an actuation mechanism for a stiffener and thus should not be considered limiting thereof. Additional embodiments and configurations of actuation mechanisms for a stiffener are further described throughout this application.

Figure 7:
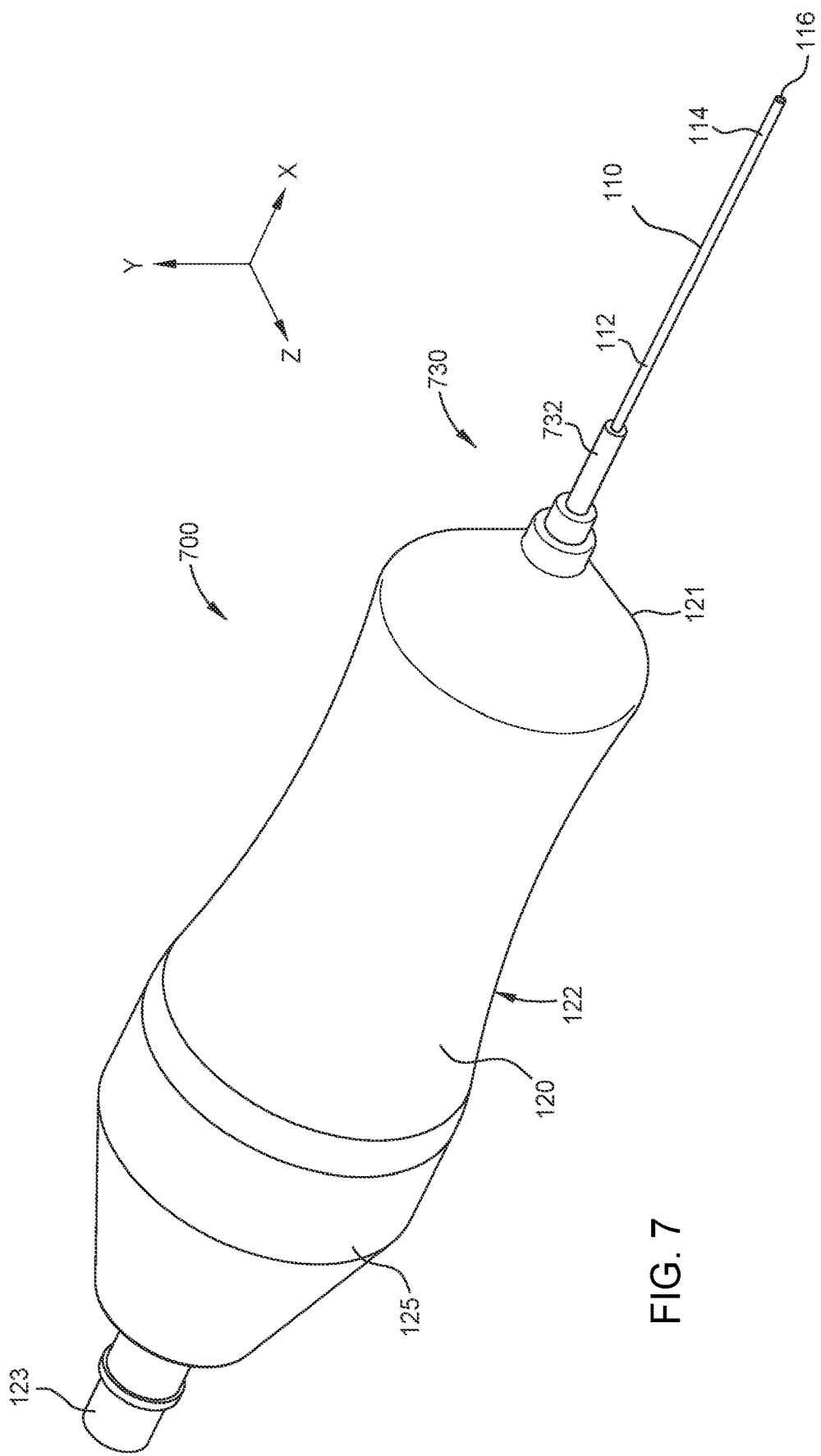
FIG. 7 illustrates a perspective view of an exemplary instrument according to one embodiment of the present disclosure.

FIG. 7 illustrates a perspective view of another exemplary instrument 700 according to one embodiment described herein. The instrument 700 is substantially similar to the instruments 100, 300, and 500, except for the structure and actuating mechanism of stiffener assembly 730 (shown in FIGS. 8A and 8B). The stiffener assembly 730 is a self-adjusting stiffener assembly and includes a stiffener 732 coupled to a biasing device 738. FIGS. 8A and 8B illustrate schematic cross-sectional views of the instrument 700 with the stiffener 732 positioned at different points along the length L of the probe 110, and thus, are herein described together with FIG. 7 for clarity.

Similar to the stiffeners 132, 332, and 532 described above, the stiffener 732 is generally a hollow tube slidably mounted to and substantially surrounding the probe 110 at the proximal portion 112. The stiffener 732 is disposed through the opening 117 in the base unit 120 and extends into the interior chamber 124 thereof. In one embodiment, the stiffener 732 includes an annular flange (e.g., flange 736) disposed at a proximal end (e.g., proximal end 733) within the interior chamber 124. In other embodiments, the flange 736 is disposed more axially along a length of the stiffener 732. The flange 736 is configured to prevent the stiffener 732 from completely sliding through the opening 117 and out of the base unit 120. Thus, the flange 736 acts as an anchor in one capacity. In some embodiments, the flange 736 further provides a coupling surface between the stiffener 732 and the biasing device 738.

The biasing device 738 applies a biasing force against the stiffener 732 in a distal direction to urge the stiffener 732 towards a protracted position P along the length L of the probe 110. Thus, without an application of a force in an opposite, proximal direction, the stiffener 732 is constantly disposed in the protracted position P. During use, the probe 110 may be inserted into an insertion cannula with a hub (e.g., including a valve), at a desired depth along the length L selected by the user. Upon a distal end 731 of the stiffener 732 reaching the hub of the insertion cannula, the user may further press the instrument 700 towards the hub to drive the probe 110 deeper therein. Application of a force against the hub greater than that of the force provided by the biasing device 738 will cause the stiffener 732 to retract into the base unit 120 (shown in FIG. 8B), allowing a greater portion of the probe 110 to enter the eye. Accordingly, a maximum amount of support is constantly applied by the stiffener 732 to the probe 110 while the probe 110 is the only component of the instrument 700 to enter the cannula and the eye. Thus, no manual adjustment is necessary to adjust the position of the stiffener 732, and an optimal rigidity or stiffness is provided to the probe 110 at all times.

In some embodiments, the stiffener 732 is adjustable up to a distance of about 10 mm along the length L of the probe 110, such as a distance up to about 6 mm along the length L of the probe 110. For example, the stiffener 732 is adjustable up to a distance of about 3 mm along the length L of the probe 110.

In one embodiment, the biasing device 738 is actuated by a spring 739, such as a compression spring. For example, the biasing device 738 may be actuated by a coil or helical spring. In other examples, the biasing device 738 may include spring configurations other than coils. In one embodiment, the biasing device 738 is actuated by a compressible and expandable polymeric or elastomeric material. In yet another embodiment, the biasing device is actuated by a pneumatic or hydraulic piston.

Although the stiffener assembly 730 is depicted and described as having the biasing device 738, this element comprises only one embodiment of an actuation mechanism for a stiffener and thus should not be considered limiting thereof. Additional embodiments and configurations of actuation mechanisms for a stiffener are further described throughout this application.

In summary, embodiments of the present disclosure include structures and mechanisms for adjusting the stiffness of microsurgical instruments, such as small-gauge instruments for minimally-invasive ophthalmologic operations. The instruments described above include embodiments wherein a user, such as a surgeon, may adjust the stiffness of the instruments during use thereof. Accordingly, the described embodiments enable a surgeon to access a wider range of tissues with a single instrument, thus expanding the applicability of smaller gauge instruments to a greater range of indications.

In one example, the described embodiments enable a surgeon to dynamically adjust the stiffness and length of a vitrectomy probe to access all areas of a vitreous cavity during a single procedure. The adjustment of the probe may be carried out prior to insertion of the probe into the eye or after the probe has already been inserted therein. Thus, the described embodiments may be utilized to facilitate access to the posterior segment of an eye during vitreous surgeries while retaining the benefits of smaller gauge probes, such as increased patient comfort, less conjunctival scarring, less postoperative inflammation, and faster healing time. Although vitreous surgery is discussed as an example of a surgical procedure that may benefit from the described embodiments, the advantages of an instrument with adjustable stiffness may benefit other surgical procedures as well.

While the foregoing is directed to embodiments of the present disclosure, other and further embodiments of the disclosure may be devised without departing from the basic scope thereof, and the scope thereof is determined by the claims that follow.

What is claimed is:

1. A surgical instrument, comprising:
 a base unit, the base unit configured to be held by a user;
 a probe disposed through a first opening in a distal end of the base unit, the probe having a length parallel to a longitudinal axis thereof;
 a stiffener assembly, the stiffener assembly comprising:
  a stiffener disposed through the first opening in the base unit, the stiffener formed of a hollow tubular member slidably coupled to and surrounding at least a portion of the probe; and
  an actuation mechanism configured to move the stiffener along the length of the probe, wherein the actuation mechanism comprises:
   a biasing device configured to apply a biasing force against the stiffener in a distal direction,
   a housing surrounding the biasing device, wherein:
    the housing is positioned inside the base unit and extending through an interior portion of the distal end of the base unit,
    the housing separates the biasing device from an inner cavity of the base unit, and
    the inner cavity separates the housing from an inner surface of the base unit.

2. The surgical instrument of claim 1, wherein sliding the stiffener towards a distal end of the probe, exterior to the base unit, increases a rigidity of the probe.

3. The surgical instrument of claim 1, wherein an application of an opposing force in a proximal direction will retract the stiffener into the base unit.

4. The surgical instrument of claim 3, wherein the biasing device comprises a compression spring.

5. The surgical instrument of claim 4, wherein the stiffener comprises a flange at a proximal end of the stiffener, and wherein the compression spring is configured to act upon the flange in a distal direction.

6. The surgical instrument of claim 5, wherein the flange is configured prevent at least a portion of the stiffener from sliding distally past the first opening.

7. The surgical instrument of claim 3, wherein the biasing device comprises a compressible and expandable polymeric material.

8. The surgical instrument of claim 3, wherein the biasing device comprises a pneumatic or hydraulic piston.

9. The surgical instrument of claim 1, wherein the actuation mechanism includes a flange, the flange extending a width of a biasing device interior portion thereby providing a coupling surface coupling the stiffener to the actuation mechanism.

10. A surgical instrument, comprising:
a base unit, the base unit configured to be held by a user;
a probe disposed through a first opening in a distal end of the base unit, the probe having a length parallel to a longitudinal axis thereof;
a self-adjusting stiffener assembly, the self-adjusting stiffener assembly comprising:
a stiffener disposed through the first opening in the base unit, the stiffener formed of a hollow tubular member slidably coupled to and surrounding at least a portion of the probe; and
an actuation mechanism configured to move the stiffener distally along the length of the probe, wherein the actuation mechanism comprises:
a biasing device configured to apply a biasing force against the stiffener in a distal direction,
a housing surrounding the biasing device and extending through an interior portion of the distal end of the base unit, wherein:
the housing is positioned inside the base unit,
the housing separates the biasing device from an inner cavity of the base unit, and
the inner cavity separates the housing from an inner surface of the base unit.

11. The surgical instrument of claim 10, wherein translation of the stiffener towards a distal end of the probe increases a rigidity of the probe.

12. The surgical instrument of claim 10, wherein an application of an opposing force greater than the biasing force in a proximal direction will retract the stiffener into the base unit.

13. The surgical instrument of claim 10, wherein the biasing device comprises a compression spring.

14. The surgical instrument of claim 13, wherein the stiffener comprises a flange at a proximal end of the stiffener, and wherein the compression spring is configured to act upon the flange in a distal direction.

15. The surgical instrument of claim 14, wherein the flange is configured prevent at least a portion of the stiffener from sliding distally past the first opening.

16. The surgical instrument of claim 10, wherein the biasing device comprises a compressible and expandable polymeric material.

17. The surgical instrument of claim 10, wherein the biasing device comprises a pneumatic or hydraulic piston.

18. A surgical instrument, comprising:
a base unit, the base unit configured to be held by a user;
a probe disposed through a first opening in a distal end of the base unit, the probe having a length parallel to a longitudinal axis thereof;
a self-adjusting stiffener assembly, the self-adjusting stiffener assembly comprising:
a stiffener disposed through the first opening in the base unit, the stiffener formed of a hollow tubular member slidably coupled to and surrounding at least a portion of the probe, the stiffener comprising a flange at a proximal end of the stiffener; and
an actuation mechanism configured to move the stiffener along the length of the probe, wherein the actuation mechanism comprises:
a biasing device configured to apply a biasing force against the stiffener in a distal direction,
a housing surrounding the biasing device and extending through an interior portion of the distal end of the base unit, wherein:
the housing is positioned inside the base unit,
the housing separates the biasing device from an inner cavity of the base unit, and
the inner cavity separates the housing from an inner surface of the base unit.

19. The surgical instrument of claim 18, wherein the biasing device comprises a compression spring.

\* \* \* \* \*